US00PP32843P2

(12) United States Plant Patent
von Tubeuf

(10) Patent No.: US PP32,843 P2
(45) Date of Patent: Feb. 23, 2021

(54) ***BIDENS* PLANT NAMED 'KLEBF19001'**

(50) Latin Name: *Bidens ferulifolia*
Varietal Denomination: KLEBF19001

(71) Applicant: Klemm+Sohn GmbH & Co. KG, Stuttgart (DE)

(72) Inventor: Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/885,416

(22) Filed: May 28, 2020

(51) Int. Cl.
*A01H 5/02* (2018.01)
*A01H 6/14* (2018.01)

(52) U.S. Cl.
USPC ..... Plt./410

(58) Field of Classification Search
USPC ..... Plt./410
See application file for complete search history.

*Primary Examiner* — Susan McCormick Ewoldt
(74) *Attorney, Agent, or Firm* — Weatherly IP Solutions, LLC; James Weatherly

(57) ABSTRACT

A new *Bidens* plant particularly distinguished by yellow flowers with a small foliage and a very compact vigor, is disclosed.

1 Drawing Sheet

Genus and species: *Bidens ferulifolia.*
Variety denomination: 'KLEBF19001'.

BACKGROUND OF THE NEW PLANT

The present invention comprises a new and distinct variety of *Bidens*, botanically known as *Bidens ferulifolia* and hereinafter referred to by the variety name 'KLEBF19001'. 'KLEBF19001' originated from a controlled-cross between the commercial female *Bidens* variety 'KLEBF15323' (U.S. Plant Pat. No. 27,764) and the commercial male *Bidens* variety 'Bidy Gonzales Top' (unpatented).

In July 2014, the two *Bidens* parental lines 'KLEBF15323' and 'Bidy Gonzales Top' were crossed in Stuttgart, Germany and seeds were obtained. The seeds were sown and plants were grown for evaluation. A plant line was selected in April 2015 and subsequently named 'KLEBF19001'. In May 2015 'KLEBF19001' was first vegetatively propagated by vegetative cuttings in Stuttgart, Germany. 'KLEBF19001' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Yellow flowers;
2. Small foliage size; and
3. A compact plant vigor.

DESCRIPTION OF THE PHOTOGRAPH

This new *Bidens* plant is illustrated by the accompanying photograph which shows an overall view of the plant. The photograph is of an approximately 11-week-old plant grown in Stuttgart, Germany in May 2019. The colors shown are as true as can be reasonably obtained by conventional photographic procedures.

DESCRIPTION OF THE NEW VARIETY

The following detailed descriptions set forth the distinctive characteristics of 'KLEBF19001'. The data which define these characteristics were collected from asexual reproductions carried out in Stuttgart, Germany. Data was collected on plants grown 4-months old in Stuttgart, Germany grown in a greenhouse in May 2019. Color references are to The R.H.S. Colour Chart of The Royal Horticultural Society of London (R.H.S.), 5$^{th}$ edition (2007).

Classification:
- *Family.*—Asteraceae.
- *Botanical.*—*Bidens ferulifolia.*
- *Designation.*—'KLEBF19001'.

Parentage:
- *Female parent.*—The commercial female *Bidens* variety 'KLEBF15323' (U.S. Plant Pat. No. 27,764).
- *Male parent.*—The commercial male *Bidens* variety 'Bidy Gonzales Top' (unpatented).

Plant:
- *Habit.*—Semi-upright.
- *Height.*—7.0 cm.
- *Spread.*—13.0 cm.
- *Life cycle.*—Annual.
- *Form.*—Round.
- *Time to produce a rooted cutting.*—4 weeks.
- *Root description.*—Fine, white.
- *Rooting habit.*—Freely branching.
- *Time to bloom from propagation.*—8 weeks from potting date.
- *Branching habit.*—Freely branching.

Lateral branches:
- *Quantity per plant.*—6 to 8.
- *Color.*—RHS 145B.
- *Pubescence.*—Present.
- *Diameter.*—0.2 cm.
- *Length.*—3.0 cm to 5.0 cm.
- *Internode length.*—1.0 cm to 2.0 cm.
- *Anthocyanin.*—Absent.

Leaves:
- *Arrangement.*—Opposite.
- *Length.*—1.5 cm to 3.0 cm.

*Width.*—2.0 cm to 2.5 cm.
*Shape.*—Composed.
*Apex.*—Obtuse.
*Base.*—Acute.
*Margin.*—Pinnate.
*Texture.*—Upper surface: Smooth. Lower surface: Smooth.
*Venation pattern.*—Pinnate.
*Color of developing leaves (immature).*—Upper surface: RHS 143A. Lower surface: RHS 143C. Venation color: Upper surface: RHS 144C. Lower surface: Not applicable.
*Color of fully expanded leaves (mature).*—Upper surface: RHS N137B. Lower surface: RHS N137C. Venation color: Upper surface: RHS 144C. Lower surface: RHS N137B.
*Petiole.*—Length: 0.5 cm to 1.0 cm. Diameter: 0.15 cm. Color: RHS 143A. Texture: Slightly pubescent.

Inflorescence:
*Appearance.*—Daisy-type.
*Flowering habit.*—Continuously.
*Lastingness of inflorescence on the plant.*—6 to 7 days.
*Number of inflorescences and buds per plant.*—3 inflorescences and 2 to 3 buds at time of maturity.
*Fragrance.*—Present.
*Natural flowering season.*—Spring through summer.
*Diameter.*—5.5 cm.
*Depth.*—0.7 cm.
*Disc diameter.*—1.0 cm.

Flower buds:
*Length.*—0.5 cm.
*Diameter.*—0.5 cm.
*Surface texture.*—Pubescent.
*Shape.*—Ovate.
*Color.*—RHS N137C with 145C (thin stripes and center between immature petals).

Ray florets:
*Quantity per inflorescence.*—7 to 8.
*Length.*—About 2.5 cm.
*Width.*—About 1.5 cm.
*Shape.*—Ovate.
*Apex.*—Tridentate.
*Base.*—Ovate.
*Margin.*—Entire.
*Color, when opening.*—Upper surface: RHS 9A. Lower surface: RHS 9A.
*Color, when fully open.*—Upper surface: RHS 9A. Lower surface: RHS 9A.
*Surface texture (both upper and lower surfaces).*—Smooth.

Disc florets:
*Quantity per inflorescence.*—About 70.
*Length.*—0.7 cm.
*Width.*—0.8 cm.
*Shape.*—Tubular.
*Apex.*—Five-pointed.
*Base.*—Fused.
*Margin.*—Entire.
*Color, when fully open.*—Upper surface: Not applicable (too small to define). Lower surface: Not applicable (too small to define).
*Surface texture (both upper and lower surfaces).*—Smooth.

Phyllaries:
*Quantity per inflorescence.*—13, not including the calyx.
*Length.*—0.4 cm to 0.6 cm.
*Width.*—0.15 cm to 0.2 cm when measured at the base.
*Shape.*—Lanceolate.
*Apex.*—Acute.
*Base.*—Truncate.
*Margin.*—Entire.
*Surface texture.*—Upper surface: Smooth. Lower surface: Pubescent.
*Color.*—Upper surface: RHS 137B. Lower surface: RHS 137B.

Calyx:
*Length.*—0.5 cm to 0.6 cm.
*Width.*—0.2 cm.
*Shape.*—Spathulate.
*Apex.*—Acute.
*Base.*—Truncate.
*Margin.*—Entire.
*Surface texture.*—Upper surface: Smooth. Lower surface: Smooth.
*Color (both surfaces).*—RHS N137B.

Peduncle:
*Length.*—About 4.0 cm.
*Diameter.*—0.1 cm.
*Color.*—RHS 143A.
*Texture.*—Medium.

Reproductive organs:
*Androecium.*—Present on disc florets only. Quantity of stamens per floret: 5. Filament length: 1.0 cm. Anther length: 0.1 cm to 0.15 cm. Pollen amount: Moderate. Pollen color: RHS 17A.
*Gynoecium.*—Present on disc florets only. Quantity of pistils per floret: 1. Pistil length: 0.4 cm. Style length: 0.25 cm. Ovary color: Not observed.

Fruit and seed set: None observed.
Disease and pest/insect resistance: None observed.

COMPARISON WITH PARENTAL LINES AND KNOWN VARIETY

'KLEBF19001' is distinguished from its parents as described in Table 1:

TABLE 1

Comparison with Parental Lines

| Trait | 'KLEBF19001' | Female parent 'KLEBF15323' | Male parent 'Bidy Gonzales Top' |
|---|---|---|---|
| Peduncle length | Short | Long | Medium |
| Foliage size | Small | Large | Medium |
| Petal width | Wider | Less Wide | Less wide |

'KLEBF19001' can be compared to the commercial variety 'Bidy Boom Yellow Big'(not patented). Differences between the two varieties are described in Table 2:

TABLE 2

Comparison with Similar Variety

| Trait | 'KLEBF19001' | Commercial line 'Bidy Boom Yellow Big' |
|---|---|---|
| Foliage size | Smaller | Much larger |
| Vigour | Very compact | Compact-medium |

I claim:

1. A new and distinct variety of *Bidens* plant named 'KLEBF19001' as illustrated and described herein.

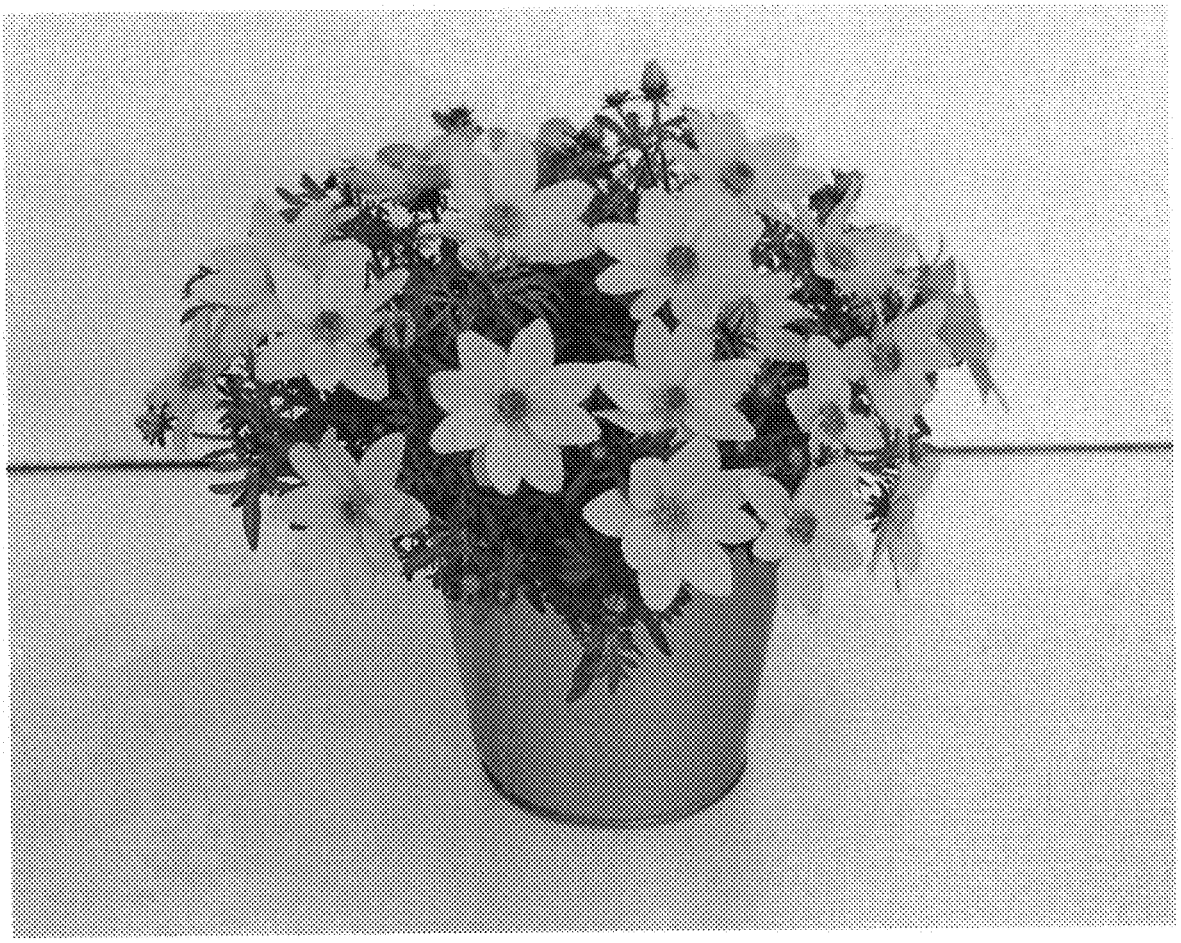

* * * * *